United States Patent [19]
Miller et al.

[11] Patent Number: 5,939,049
[45] Date of Patent: Aug. 17, 1999

[54] CHEWING STICK MADE FROM NATURAL FIBERS

[75] Inventors: Steven Eric Miller, Skillman; Alexander J. Simone, Somerset, both of N.J.

[73] Assignee: Colgate-Palmolive Company, New York, N.Y.

[21] Appl. No.: 08/728,987

[22] Filed: Oct. 11, 1996

[51] Int. Cl.$^6$ .............................. A61K 7/16; A61K 7/18; A61K 6/00; A61K 7/00

[52] U.S. Cl. .............................. 424/49; 424/52; 424/401; 424/673; 514/635; 514/643; 514/721

[58] Field of Search .............................. 424/49, 52, 401, 424/673, DIG. 5; 514/635, 643, 721

[56] References Cited

U.S. PATENT DOCUMENTS

| | | | |
|---|---|---|---|
| 792,471 | 6/1905 | Smith . | |
| 1,520,491 | 12/1924 | Weissleder . | |
| 2,160,731 | 5/1939 | Haeberlin | 32/58 |
| 2,244,336 | 6/1941 | Horn | 91/62.5 |
| 2,581,561 | 1/1952 | Shaw | 18/56 |
| 2,887,340 | 5/1959 | Veneko | 300/21 |
| 3,071,476 | 1/1963 | Werft et al. | 99/135 |
| 3,217,074 | 11/1965 | Gould et al. | 264/210 |
| 3,577,839 | 5/1971 | Charvat et al. | 15/179 |
| 3,613,143 | 10/1971 | Muhler et al. | 15/167 |
| 3,618,609 | 11/1971 | Glick, et al. | 128/296 |
| 3,853,412 | 12/1974 | Griffin | 401/183 |
| 4,144,610 | 3/1979 | Moore et al. | 15/159 |
| 4,149,815 | 4/1979 | Kawam | 401/201 |
| 4,188,429 | 2/1980 | Braconnier et al. | 428/85 |
| 4,387,480 | 6/1983 | Cobianco | 15/169 |
| 4,391,665 | 7/1983 | Mitchell, Jr. et al. | 156/72 |
| 4,462,136 | 7/1984 | Nakao et al. | 15/167 |
| 4,554,154 | 11/1985 | White | 424/16 |
| 4,616,374 | 10/1986 | Novogrodsky | 15/167 |
| 4,646,381 | 3/1987 | Weihrauch | 15/167 |
| 4,748,709 | 6/1988 | Oates | 15/104 |
| 5,373,599 | 12/1994 | Lemon et al. | 15/104 |
| 5,407,661 | 4/1995 | Simone et al. | 424/49 |
| 5,413,127 | 5/1995 | Hill | 132/321 |
| 5,445,825 | 8/1995 | Copelan et al. | 424/448 |

FOREIGN PATENT DOCUMENTS

| | | |
|---|---|---|
| 623779 | 6/1927 | France . |
| 829142 | 6/1938 | France . |
| 2539283 | 7/1984 | France . |
| 4417548 | 11/1995 | Germany . |
| 55-90269 | 7/1980 | Japan . |
| 479277 | 11/1969 | Switzerland . |
| 1340735 | 9/1987 | U.S.S.R. . |
| 490124 | 9/1938 | United Kingdom . |
| 2137080 | 10/1984 | United Kingdom . |

OTHER PUBLICATIONS

Addo–Yobo, C., Williams, S.A., Curzon, M.E.J., Oral Hygiene Practices, Oral Cleanliness and Periodontal Treatment Needs in 12–Year Old Urban and Rural School Children in Ghana, Community Dental Health, 8:155–162, 1990.

Butt, M.H., Dunning, J.M., Reimplementation of Chewing Stick Oral Hygiene in Kenya, Odontostomatol. Trop. 9:35–37, 1986.

Clerehugh, V., Laryea, U., Worthington, H.V., Periodontal Condition and Comparison of Toothcleaning Using Chewing Sponge, Chewing Sticks and Toothbrushes in 14–Year–Old School Children in Ghana, Community Dentistry and Oral Epidemiology, 23:319–320, 1995.

Danielsen, B., Baelum, V., Manji, F., Fejerskov, O., Chewing Sticks, Toothpaste and Plaque Removal, Acta Odontol. Scand. 47:121–125, 1989.

Khoory, T. The Use of Chewing Sticks in Preventive Oral Hygiene, Journal of Clinical Preventive Dentistry, 5:11–14, 1983.

Manley, J.L., Limongelli, W.A., Williams, A.C., The Chewing Stick: Its Uses and Relationship to Oral Health, Journal of Preventive Dentistry, 2:7–9, 1975.

Norton, M.R., Addy, M., Chewing Sticks Versus Toothbruses in West Africa: A Pilot Study, Journal of Clinical Preventive Dentistry, 11:11–13, 1989.

Parajas, I.L., The Effectiveness and Acceptability of Indigenous Toothbrush Materials Among School Children in Aguinaldo, Cavite, Odontostomatol. Trop., 10:115–119, 1987.

*Primary Examiner*—Kimberly Jordan
*Attorney, Agent, or Firm*—Richard Ancel; Henry Goldfine

[57] ABSTRACT

A natural fiber chewing stick including a plurality of strips of treated natural fibers bonded together, said strips including flavor and other compositions added during processing. Typically, the individual strips used are of jute, but other natural fibers may be used.

5 Claims, 1 Drawing Sheet

CHEWING STICK MADE FROM NATURAL FIBERS

BACKGROUND OF THE INVENTION

This invention relates to chewing sticks made from natural fibers, such as jute fibers. Natural fiber chewing sticks of jute are known, and include whatever ingredients, such as flavors, which are natural to them.

SUMMARY OF THE INVENTION

A natural fiber, stick-like device which is chewed briefly and used to brush and clean the teeth. The device is used in a fashion similar to natural, non-synthetic chewing sticks used for oral hygiene in many developing countries but provides several improvements over these natural sticks.

DETAILED DESCRIPTION OF THE INVENTION

Figure 1:
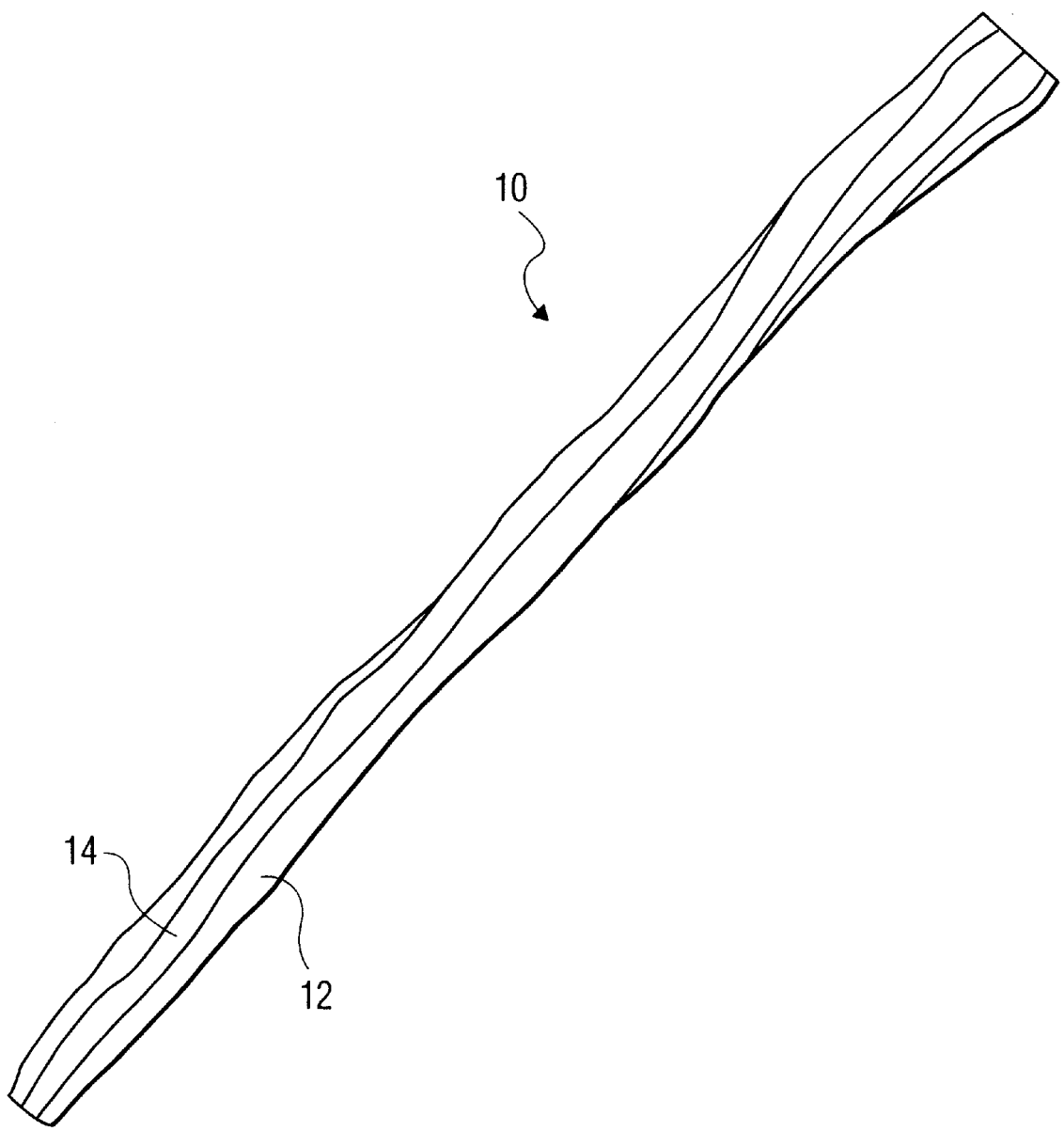
FIG. 1 is a perspective view of the chewing device of this invention.

A synthetic chewing stick 10 has been developed using the following method of preparation. Raw jute which has been processed by soaking in water and shredding into long fiber elements or pieces such as 12 and 14 are used. Sections of raw jute are cut into 5–8 inch lengths. A gel phase containing 3% xanthan (Kelco K4B351), 1% flavor oil and 96% water is prepared. The raw jute is soaked in the gel until all fibers are wet. Excess gel is removed, the individual sections of fiber are formed into a stick of desired thickness (0.5–2 cm) and heated until dry and stiff (140° C./1 hour). The stick 10 must be fully dried to result in a stiff stick. If necessary, the dried sticks are oversprayed with additional flavor oil to enhance the flavor impact during use. 6 kg of gel phase was used to prepare 600–650 sticks. When one end is chewed the fiber quickly softens into a brush for cleaning all teeth surfaces. Actives and flavor present are released during the cleaning process. After use, the stick is allowed to dry and the chewed end rehardens. This end can be reused or cut off as desired. This can be continued until the stick is too short to easily handle.

Alternate natural fibers such as hemp, sisal, ramie, kenal, flax, roselle, sunn, orena, abaca, cantala, caroa, henequen, istle, mauritis, phormium, pineapple, sansevieria, coir, cotton, kapok, milkweed floss, broom root, broom corn, crin vegetal, palmyra palm, pissava, raffia or other commercial plant fibers could be used. Alternate binders such as cellulose and starch products, inorganic materials such as dicalcium phosphate, sugars and sorbitols, tragacanth, carbowax, plasdone or other commercial binders could be used. The device may include flavor oil, other plant derived oils such as neem (and other herbal extracts), therapeutic agents such as fluoride, CPC, BTC, chlorhexidene, triclosan and preservatives such as BTC, may be added.

Improvements over the natural stick include ease of use, better breath freshening and better therapeutic oral care. Because the fibers soften in seconds of chewing, the extensive, time-consuming chewing necessary to form a brush-like end from a natural stick is not required. The inclusion of flavor oils provides improved fresh breath compared to the natural stick. The inclusion of therapeutic levels of active ingredients such as fluoride, anti-microbials, anti-inflammatory agents will result in improved therapeutic benefit. Inclusion of a preservative will result in improved oral hygiene with a device which is reused. In general the chewing stick will allow individuals to continue using a low cost device which is similar to what they are familiar with and accustomed to while enjoying many of the oral hygiene benefits of modern therapeutic oral care products such as toothpastes and mouth rinses.

A number of agents may be used as binders including hydroxypropyl cellulose, guar gum, gum arabic, locust bean gum, potato starch and gelatin. None resulted in a firm, stiff stick comparable to the xanthan binder. The fiber may could be varied among a number of natural fibers such as jute, hemp or sisal or types of plastic fiber could be used.

Because this stick can incorporate flavor and active ingredients, it provides improved breath freshening and therapeutic benefits not found in the natural chewing stick. The product is also more convenient to use because a brush like end can be formed very quickly compared to the natural version.

We claim:

1. A chewing stick for brushing and cleaning the teeth, which forms a brush-like edge after chewing, comprised of natural fibers which have been separated into a plurality of fiber elements or pieces of predetermined length and bonded together in parallel by a binder, wherein said binder is selected from the group consisting of xanthan, cellulose, dicalcium phosphate, sugar, sorbitol, tragacanth, carbowax, plasdone, and mixtures thereof, said chewing stick further comprised of ingredients selected from the group consisting of flavor oils, therapeutic agents, preservatives and mixtures thereof.

2. The stick of claim 1 wherein said natural fibers are selected from the group consisting of jute, hemp, sisal, ramie, kenal, flax, roselle, sunn, orena, abaca, cantala, caroa, henequen, istle, mauritis, phormium, pineapple, sansevieria, coir, cotton, kapok, milkweed floss, broom root, broom corn, crin vegetal, palmyra palm, pissava, and raffia, or mixtures thereof.

3. The stick of claim 1 wherein said natural fibers are of jute.

4. The stick of claim 1 wherein said therapeutic agents are selected from the group consisting of fluoride, chlorhexidene, triclosan, and mixtures thereof.

5. The stick of claim 1 wherein said strips include a preservative.

* * * * *